United States Patent
Paul et al.

[19]

[11] Patent Number: 6,143,033
[45] Date of Patent: Nov. 7, 2000

[54] ALLOGENIC INTERVERTEBRAL IMPLANT

[75] Inventors: David C. Paul, Drexel Hill; Hansjuerg W. Emch, Philadelphia; Beat Schenk, Paoli; Jeffrey L. Carver, Downingtown; Kelly J. Baker, Coatesville, all of Pa.

[73] Assignee: Synthes (USA), Paoli, Pa.

[21] Appl. No.: 09/219,439

[22] Filed: Dec. 23, 1998

Related U.S. Application Data

[60] Provisional application No. 60/073,271, Jan. 30, 1998, and provisional application No. 60/095,425, Aug. 5, 1998.

[51] Int. Cl.$^7$ .............................. A61F 02/44; A61F 02/28
[52] U.S. Cl. ...................... 623/17.11; 623/16.11
[58] Field of Search ....................... 623/17, 16

[56] References Cited

U.S. PATENT DOCUMENTS

| | | | |
|---|---|---|---|
| 4,627,853 | 12/1986 | Campbell et al. | 623/16 |
| 4,678,470 | 7/1987 | Nashef et al. | 623/16 |
| 4,950,296 | 8/1990 | McIntyre | 623/16 |
| 5,053,049 | 10/1991 | Campbell | 623/16 |
| 5,092,893 | 3/1992 | Smith | 623/17 |
| 5,275,954 | 1/1994 | Wolfinbarger et al. | 436/74 |
| 5,306,303 | 4/1994 | Lynch | 623/16 |
| 5,306,308 | 4/1994 | Gross et al. | 623/17 |
| 5,514,180 | 5/1996 | Heggeness et al. | 623/17 |
| 5,534,030 | 7/1996 | Navarro et al. | 623/17 |
| 5,556,379 | 9/1996 | Wolfinbarger | 604/49 |
| 5,609,637 | 3/1997 | Biedermann et al. | 623/17 |
| 5,658,337 | 8/1997 | Kohrs et al. | 623/17 |
| 5,702,449 | 12/1997 | McKay | 623/17 |
| 5,702,455 | 12/1997 | Saggar | 623/17 |
| 5,722,977 | 3/1998 | Wilhelmy | 606/84 |
| 5,725,579 | 3/1998 | Fages et al. | 623/16 |
| 5,728,159 | 3/1998 | Stroever et al. | 623/16 |
| 5,741,253 | 4/1998 | Michelson | 606/61 |
| 5,766,253 | 6/1998 | Brosnahan, III | 623/17 |
| 5,776,199 | 7/1998 | Michelson | 623/17 |
| 5,785,710 | 7/1998 | Michelson | 606/61 |
| 5,797,871 | 8/1998 | Wolfinbarger, Jr. | 604/49 |
| 5,814,084 | 9/1998 | Grivas et al. | 623/16 |
| 5,820,581 | 10/1998 | Wolfinbarger, Jr. | 604/49 |
| 5,865,845 | 2/1999 | Thalgott | 623/17 |
| 5,888,222 | 3/1999 | Coates et al. | 623/17 |
| 5,888,227 | 3/1999 | Cottle | 623/17 |
| 5,897,593 | 4/1999 | Kohrs et al. | 623/17 |
| 5,972,368 | 10/1999 | McKay | 424/423 |
| 5,989,289 | 11/1999 | Coates et al. | 623/17 |

FOREIGN PATENT DOCUMENTS

| | | | |
|---|---|---|---|
| 000538183 | 4/1993 | European Pat. Off. | 623/17 |
| 094026213 | 2/1994 | WIPO | 623/17 |
| WO 98/17209 | 4/1998 | WIPO . | |
| WO 98/55052 | 12/1998 | WIPO . | |
| WO 98/56319 | 12/1998 | WIPO . | |
| WO 98/56433 | 12/1998 | WIPO . | |

*Primary Examiner*—Paul J. Hirsch
*Assistant Examiner*—Michael B. Priddy
*Attorney, Agent, or Firm*—Pennie & Edmonds LLP

[57] ABSTRACT

An allogenic intervertebral implant for fusing vertebrae is disclosed. The implant is an annular plug conforming in size and shape with end plates of vertebrae. The implant has either an exterior surface identical to that of the harvest bone or an exterior surface machined to have a uniform shape such as an oval or a rectangle. The top and bottom surfaces of the implant have a plurality of teeth to resist expulsion and provide initial stability. The top and bottom surfaces can be either flat planar surfaces or curved surfaces. Preferably, the anterior height of the implant is greater than the posterior height so that the implant is wedge-shaped profile to help restore disc height and the natural curvature of the spine. In one embodiment, the top and bottom surfaces each have a channel oriented in the anterior, lateral, or anterolateral direction for receiving a surgical instrument. The implant can also have a hole for attachment of an inserter. Although the interior space formed by the annular plug can be the natural shape defined by the medullary canal, the medullary canal walls can be machined so that the implant has a uniform interior space.

16 Claims, 2 Drawing Sheets

ALLOGENIC INTERVERTEBRAL IMPLANT

CROSS-REFERENCE TO RELATED APPLICATIONS

Priority of Provisional Application no. 60/073,271, filed on Jan. 30, 1998 and Provisional Application no. 60/095, 425, filed on Aug. 5, 1998 is claimed under 35 U.S.C. § 119(e).

FIELD OF THE INVENTION

The present invention is directed to an allogenic implant and, more particularly, to an allogenic intervertebral implant for use in the treatment of back pain.

BACKGROUND OF THE INVENTION

A number of medical conditions such as compression of spinal cord nerve roots, degenerative disc disease, and trauma can cause severe back pain. Intervertebral fusion is a surgical method of alleviating back pain. In intervertebral fusion, two adjacent vertebral bodies are fused together by removing the affected intervertebral disc and inserting an implant that would allow for bone to grow between the two vertebral bodies to bridge the gap left by the disc removal.

A number of different implants and implant materials have been used for fusion with varying success. Current implants used include titanium cages and allografts. Titanium cages suffer from the disadvantage of requiring drilling and tapping of the vertebral endplates for insertion. In addition, the incidence of subsidence in long term use is not known. Due to MRI incompatibility of titanium, determining fusion is problematic. Finally, restoration of lordosis, i.e., the natural curvature of the cervical and lumbar spine is very difficult when a titanium cage is used.

Allografts are sections of bone taken from the diaphysis of a long bone, such as the radius, ulna, fibula, humerus, tibia, or femur of a donor. A cross section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They are also MRI compatible so that fusion can be more accurately ascertained and promote the formation of bone, i.e., osteoconductive. Although the osteoconductive nature of the allograft provides a biological interlocking between the allograft and the vertebrae for long term mechanical strength, initial and short term mechanical strength of the interface between the allograft and the vertebrae are lacking such that there is a possibility of the allograft being expelled after implantation.

U.S. Pat. No. 5,728,159 discloses an allograft having grooves on end faces in an attempt to try to promote stability, but there are more effective ways for resisting expulsion. For example, WO 98/17209, published Apr. 30, 1998, is directed to a spinal spacer and has one embodiment which is an allograft cortical ring having teeth on superior and/or inferior surfaces. These teeth provide the initial, secure interlocking with the vertebrae.

Most allografts are simply sections of bone which, although cut to the approximate height of the disc being replaced, have not been sized and/or machined on the exterior surface to have a uniform shape. As a result, the fusion of the vertebral bodies does not occur in optimal anatomic position in a consistent manner along the surface of the endplates. While a surgeon may do some minimal intraoperative shaping and sizing to customize the allograft for the patient's anatomy, significant shaping and sizing of the allograft is not possible due to the nature of the allograft. Even if extensive shaping and sizing were possible, a surgeon's ability to manually shape and size the allograft to the desired dimensions is severely limited.

As the discussion above illustrates, there is a need for an improved allogenic implant for fusing vertebrae and relieving back pain.

SUMMARY OF THE INVENTION

The present invention relates to an allogenic intervertebral implant for use when surgical fusion of vertebral bodies is indicated. The implant comprises an annular plug conforming in size and shape with the end plates of adjacent vertebrae and has a plurality of teeth positioned on the top and bottom surfaces for interlocking with the adjacent vertebrae. The teeth preferably have a pyramid shape or a saw-tooth shape. In one embodiment, the implant has an exterior surface machined to have a uniform shape, such as an oval or a rectangle. The interior space delineated by the annular plug also can have a machined wall to provide the implant with a uniform interior space.

The top and bottom surfaces may be flat planar surfaces or curved surfaces to mimic the topography of the end plates of the adjacent vertebrae. In a preferred embodiment, the anterior height of the implant is greater than the posterior height of the implant so that the implant has a wedge-shaped profile to help restore disc height and the natural curvature of the spine.

In one embodiment, the implant has channels on the top and bottom surfaces for receiving a surgical tool. These channels can run in the anterior, lateral, or anterolateral direction to accommodate a variety of different tools used in surgical procedures. Finally, a threaded hole on the anterior, anterolateral, or lateral side can be provided for receiving a threaded arm of an insertion tool.

DESCRIPTION OF THE PREFERRED EMBODIMENTS

Figure 1:
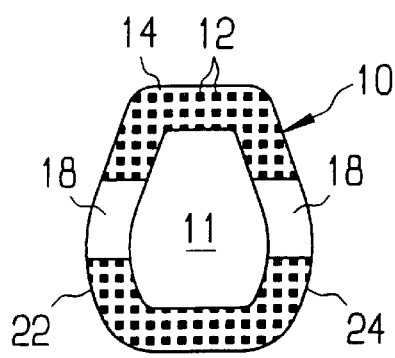
FIG. 1 is a top view of a first embodiment of the implant according to the present invention.
Figure 6:
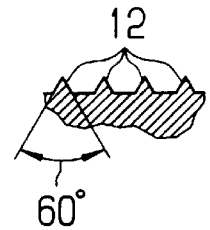
FIG. 6 is a close up of region A from FIG. 4 and FIG. 8.
Figure 10:
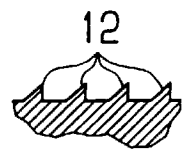
FIG. 10 shows an alternative tooth configuration.

FIG. 1 shows a top view of a first embodiment of an allogenic intervertebral implant 10 according to the present invention. Implant 10 is annular and conforms in size and shape with the end plates of the vertebrae between which implant 10 is to be implanted. Because implant 10 is annular, new bone can form in interior 11. Interior 11 can be filled with bone chips or any other osteoconductive material to promote the formation of bone. Although implant 10 will probably be predominantly used in the lumbar region of the spine, implant 10 can be configured for implantation in any region of the spine. Implant 10 has a plurality of teeth 12 on superior and inferior surfaces 14, 16 which provide a mechanical interlock between implant 10 and the end plates. These teeth 12 provide the mechanical interlock by penetrating the end plates. The initial mechanical stability afforded by teeth 12 minimizes the risk of post-operative expulsion of implant 10. Preferably, teeth 12 are pyramid-shaped in which the angle formed from the tip to the base may be between about 45 and 75° and is preferably about 60°. The details of teeth 12 are best seen in FIG. 6. The teeth provide an enhanced interlock with the adjacent vertebrae compared to the use of channels, because the teeth impale the vertebrae surfaces. In comparison, channels impart grooves into the vertebrae surfaces and the implant can slide out along the direction of the channels or grooves. In an alternative embodiment, teeth 12 have a saw-tooth shape (FIG. 10).

Figure 2:
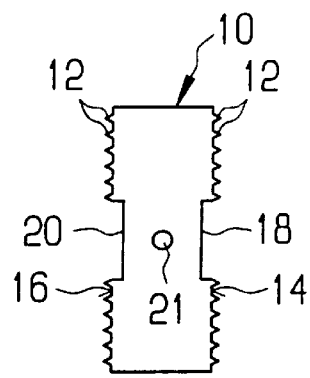
FIG. 2 is a front view of the implant of FIG. 1.

As shown in FIG. 1 and FIG. 2, superior surface 14 has a channel 18 and inferior surface 16 has a channel 20 which is parallel to channel 18. Channels 18, 20 are sized to receive a surgical instrument such as an inserter and/or distractor. As the names imply, an inserter is a surgical instrument used to insert implant 10 and a distractor is a surgical instrument used to separate the adjacent vertebrae so that the surgeon has access to the intervertebral space. If the inserter has a threaded arm, implant 10 can be provided with optional threaded hole 21. In FIG. 1 and FIG. 2, channels 18 and 20 are oriented in the anterior/posterior direction. This orientation is useful if the surgeon prefers an anterior surgical approach.

Figure 3:
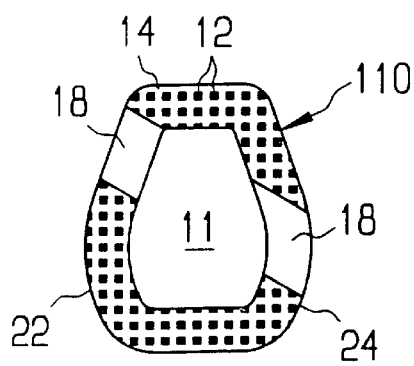
FIG. 3 is a top view of a second embodiment of the implant.

FIG. 3 shows a second embodiment of an allogenic intervertebral implant 110 according to the present invention. In general, most of the structure of implant 110 (as well as the embodiments described below) is like or comparable to the structure of implant 10 and, accordingly the same reference numeral is used for like components and discussion of those like components is not believed necessary. As shown in FIG. 3, channels 18, 20 can run in the anterolateral direction to facilitate use of implant 110 with an anterolateral surgical approach. As another alternative embodiment, channels 18, 20 could run in the lateral direction for a lateral approach. Similarly, a threaded hole 21 optionally can be located on the lateral or anterolateral side of implant 10.

Figure 4:
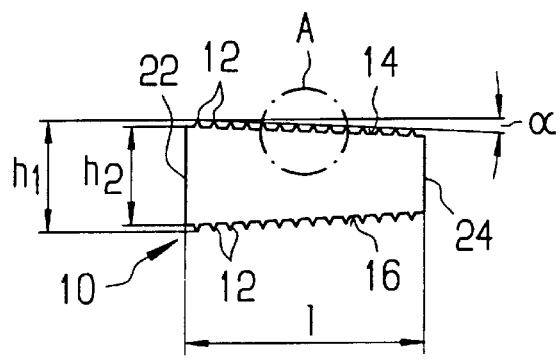
FIG. 4 is a side view of the implant of FIG. 1.

In order to restore the natural curvature of the spine after the affected disc has been removed, implant 10 is provided with a wedge-shaped profile. As shown in FIG. 4, one way to achieve this wedge shape results from a gradual decrease in height from the anterior side 22 to the posterior side 24. In anatomical terms, the natural curvature of the lumbar spine is referred to as lordosis. When implant 10 is to be used in the lumbar region, angle α should be approximately 4.2° so that the wedge shape is a lordotic shape which mimics the anatomy of the lumbar spine. Furthermore, when used in the lumbar region, the ratio of the height of anterior side 22 ($h_1$) to the height of posterior side 24 ($h_2$) should be approximately 1.1–2 with the length of implant 10 (1) being approximately 22–30 mm.

In FIG. 4, superior and inferior surfaces 14, 16 are flat planar surfaces so that if the surgeon prepares the endplates to be parallel surfaces with a burr, implant 10 fits tightly between the bone surfaces.

Figure 5:
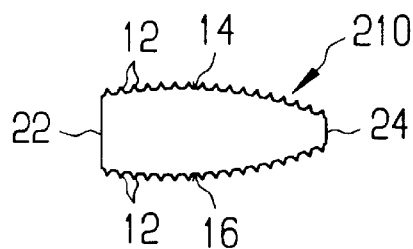
FIG. 5 is a side view of a third embodiment of the implant.

FIG. 5 illustrates that superior and inferior surfaces 14, 16 of a third embodiment of an allogenic intervertebral implant 210 can be curved surfaces and still retain the wedge-shaped profile. The curved surface of superior and inferior surfaces 14, 16 is a mirror-image of the topography of the vertebral end plates. Thus, the curved surfaces conform to the contours of the end plates.

Figure 7:
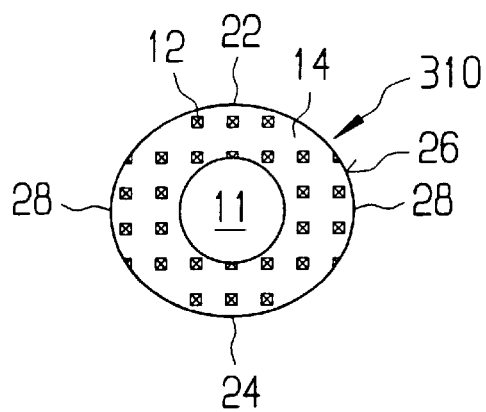
FIG. 7 is a top view of a fourth embodiment of the implant according to the present invention.

FIG. 7 shows a top view of a fourth embodiment of an allogenic intervertebral implant 310 according to the present invention. Although implant 310 will probably be predominantly used in the cervical region of the spine, implant 310 can be configured for implantation in any region of the spine. Interior 11 can be defined by the natural shape of the medullary canal as was the case for implant 10, 110, 210. Alternatively, the medullary canal can be machined so that the wall that formed interior 11 are uniform in shape and texture.

As previously noted, teeth 12 are preferably pyramid-shaped in which the angle formed from the tip to the base is preferably about 60°. Pyramid-shaped teeth help prevent expulsion of the implant in all directions. The prevention of movement between implant 310 and the vertebrae is particularly important when the surgeon removes all of the annulus fibrosis, as may be the case for cervical vertebrae.

Most allografts are processed and used without significant machining of the exterior surface. In other words, the allografts have substantially the shape of the bone from which the allograft was harvested. As shown in FIG. 7, an exterior surface 26 of implant 310 has been machined to have a uniform shape. The uniform shape promotes initial stability until biological fixation is achieved with bony fusion.

Figure 9:
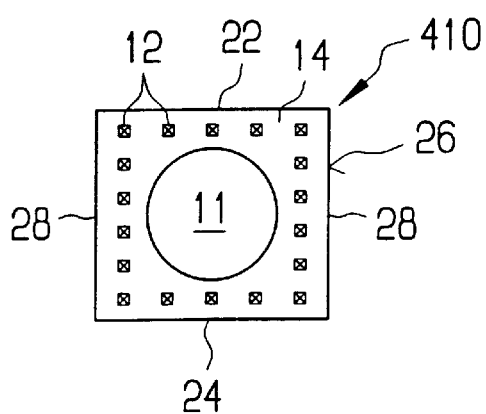
FIG. 9 is a top view of a sixth embodiment of the implant.

As shown in FIG. 7, the exterior surface 26 has an oval shape. The oval shape preferably is arranged to have lateral sides 28 along the smaller oval axis and anterior and posterior sides 22, 24 along the longer axis. In another embodiment of the invention shown in FIG. 9, the exterior surface 26 of implant 410 is rectangular in shape with lateral sides 28 shorter in length than anterior and posterior sides 22, 24. The oval and rectangle shape and size of implants 310, 410 can be made to closely match the shape and size of the affected vertebrae. Typically, lateral sides 28 and anterior and posterior sides 22, 24 would be approximately 8–18 mm in length.

Figure 8:
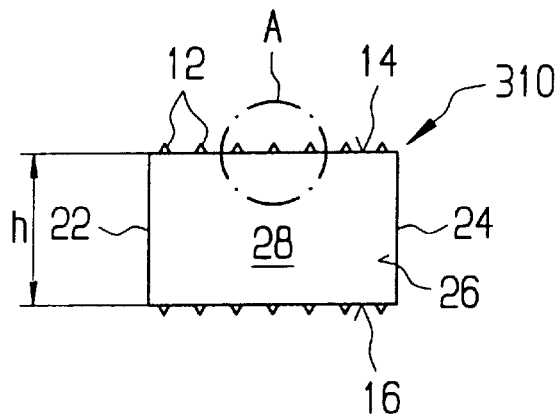
FIG. 8 is a side view of the implant of FIG. 7.

In order to restore the intervertebral space to the proper size after the affected disc has been removed, implant 310 has a height, h, sized to match the height of the removed disc, as shown in FIG. 8. The matched height helps promote fusion by providing direct contact between the bone and implant 310. Typically, h would be approximately 4–20 mm for cervical vertebrae. Implant 310 has a uniform height so that the profile of implant 310 is rectangular. Alternatively, as shown in FIG. 4 and FIG. 5, implant 310 can have a wedge shaped profile with either flat planar surfaces or curved surfaces.

It should be noted that implants 310, 410 can be configured so that h would be approximately 10–100 mm. These larger sizes could be used in corpectomy, a surgical procedure in which a section of several vertebrae is removed. Implants 310,410 would be inserted in the space created by the removed section of bone. Due to the nature of corpectomy, an accurate preoperative determination of the size of the implant needed is not possible. Thus, implant 310, 410 can be cut to the proper size by the surgeon. In such cases, the implants 310, 410 would only have teeth on either superior surface 14 or inferior surface 16.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An intervertebral implant comprising an annular plug of allogenic bone conforming in circumferential size and shape with end plates of vertebrae, wherein top and bottom surfaces of the implant include a plurality of teeth provided in a two dimensional array with the teeth being spaced apart from one another for interlocking with adjacent vertebrae, and wherein the teeth have a saw tooth shape defined by a first side extending perpendicularly to the respective top and bottom surfaces of the implant and a second side oriented at an acute angle to both the first side and the respective top and bottom surfaces of the implant.

2. The implant of claim 1, wherein the implant has a wedge-shaped profile to help restore disc height and spine curvature.

3. The implant of claim 2, having an anterior height which is greater than a posterior height to produce the wedge-shaped profile.

4. The implant of claim 1, wherein the top and bottom surfaces each have a channel for receiving a surgical instrument.

5. The implant of claim 4, wherein the channels run in an anterior-posterior direction.

6. The implant of claim 4, wherein the channels run in an anterolateral direction.

7. The implant of claim 4, wherein the channels run in a lateral direction.

8. The implant of claim 1, wherein at least one side of the implant has at least one hole for attachment of an inserter.

9. The implant of claim 8, wherein the at least one hole is threaded.

10. The implant of claim 8, wherein the at least one hole is provided in an anterior, anterolateral, or lateral side.

11. The implant of claim 1, wherein the top and bottom surfaces are parallel and are spaced by a distance that approximates that of an intervertebral disc.

12. The implant of claim 1, wherein the top and bottom surfaces are curved surfaces which are contoured to mimic the end plates of the adjacent vertebrae.

13. The implant of claim 1, wherein an exterior surface has a uniform shape.

14. The implant of claim 13, wherein the exterior surface has an oval shape.

15. The implant of claim 13, wherein the exterior surface has a rectangular shape.

16. The implant of claim 13, wherein the annular plug includes an interior surface of a machined wall.

* * * * *